United States Patent [19]

Lee

[11] Patent Number: 4,672,974
[45] Date of Patent: Jun. 16, 1987

[54] METHOD AND APPARATUS FOR "ZEROING" AND CALIBRATING A CATHETER-TIP GAUGE-PRESSURE TRANSDUCER

[76] Inventor: Arnold St. J. Lee, 1033 Hilts Ave., Los Angeles, Calif. 90024

[21] Appl. No.: 744,758

[22] Filed: Jun. 14, 1985

[51] Int. Cl.[4] .............................................. A61B 5/02
[52] U.S. Cl. .................................. 128/673; 128/748; 73/4 R; 73/740
[58] Field of Search ........................ 128/675, 672–673, 128/748; 73/723, 740, 4 R

[56] References Cited

U.S. PATENT DOCUMENTS

| | | | |
|---|---|---|---|
| 3,703,099 | 11/1972 | Rouse | 128/673 X |
| 3,831,588 | 8/1974 | Rindner | 73/723 X |
| 3,868,679 | 2/1975 | Arneson | 128/673 X |
| 3,894,535 | 7/1975 | Cannon et al. | 128/672 |
| 4,312,361 | 1/1982 | Nicholson et al. | 73/723 X |
| 4,342,218 | 8/1982 | Fox | 128/673 X |
| 4,383,431 | 5/1983 | Gelernt | 73/4 R |
| 4,384,470 | 5/1983 | Fore | 73/4 R |
| 4,413,528 | 11/1983 | Hok et al. | 128/675 X |

Primary Examiner—Kyle L. Howell
Assistant Examiner—Angela D. Sykes

[57] ABSTRACT

Sensitivity or span calibration is adjusted to a desired value by (1) noting the display indication with the reference side of the transducer at atmospheric pressure, (2) substituting a known offset pressure for atmospheric pressure on the reference side, to produce a new display indication, and (3) adjusting the display to produce that amount of displacement (between the display indications in steps 1 and 2) which corresponds to the known offset pressure multiplied by the desired calibration value.

With the sensitivity or span calibration adjusted to a desired value, the zero point of the display is adjusted by (1) independently measuring the mean of the actual pressure, (2) noting the mean value of the display indication, and (3) adjusting the zero point to eliminate discrepancy between the mean value of the display and the mean of the actual pressure.

The apparatus has a port for a substitute reference pressure, and an external pressure gauge for measuring the mean pressure through an auxiliary lumen of the catheter.

29 Claims, 7 Drawing Figures

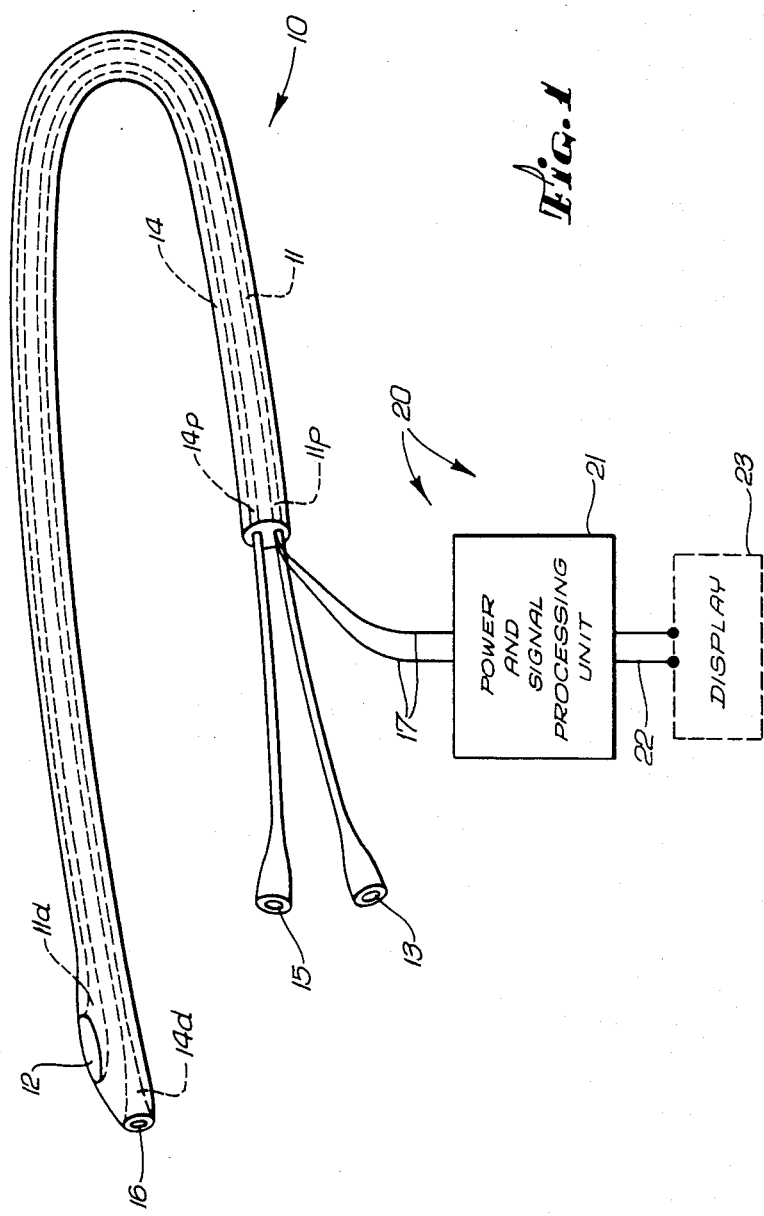

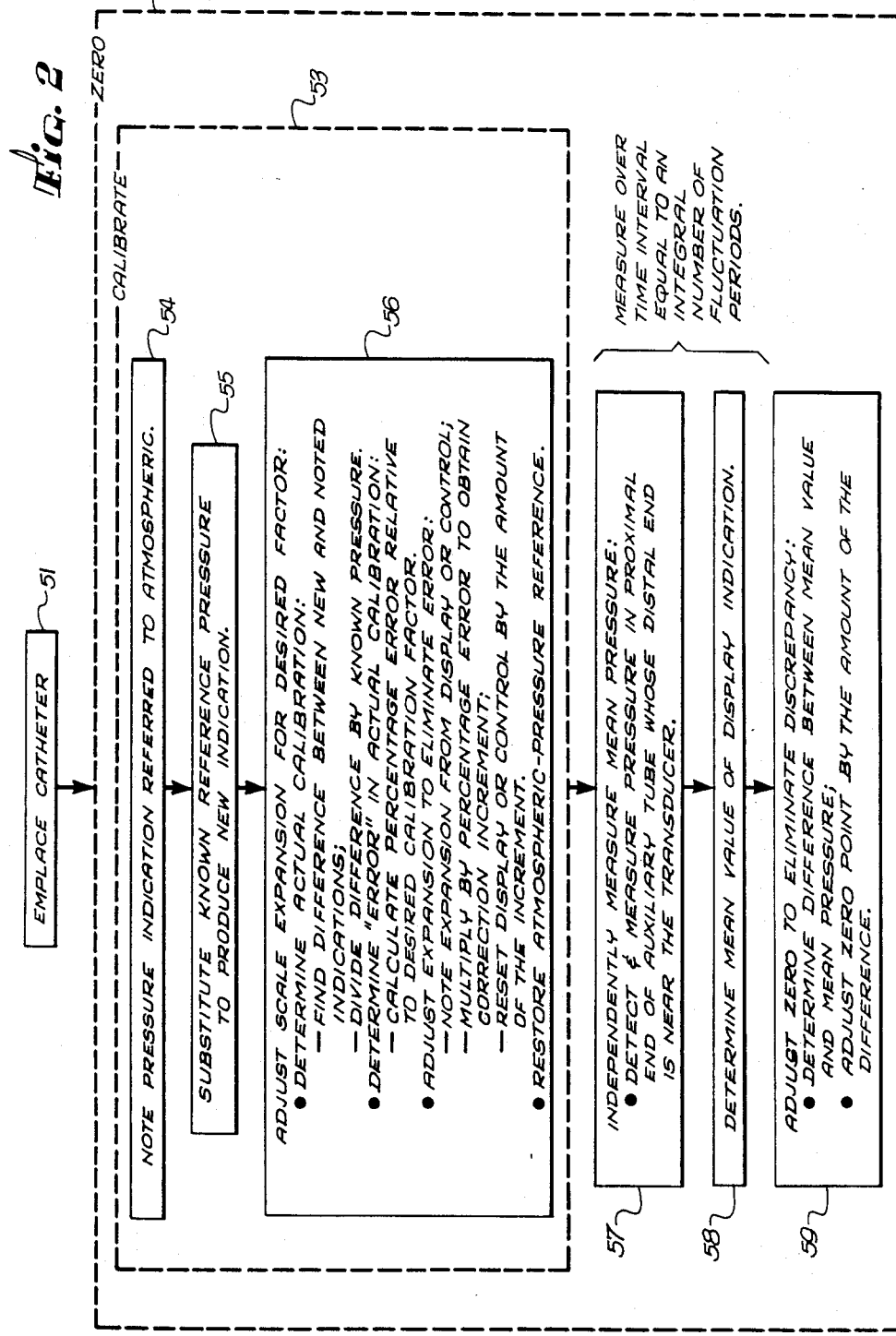

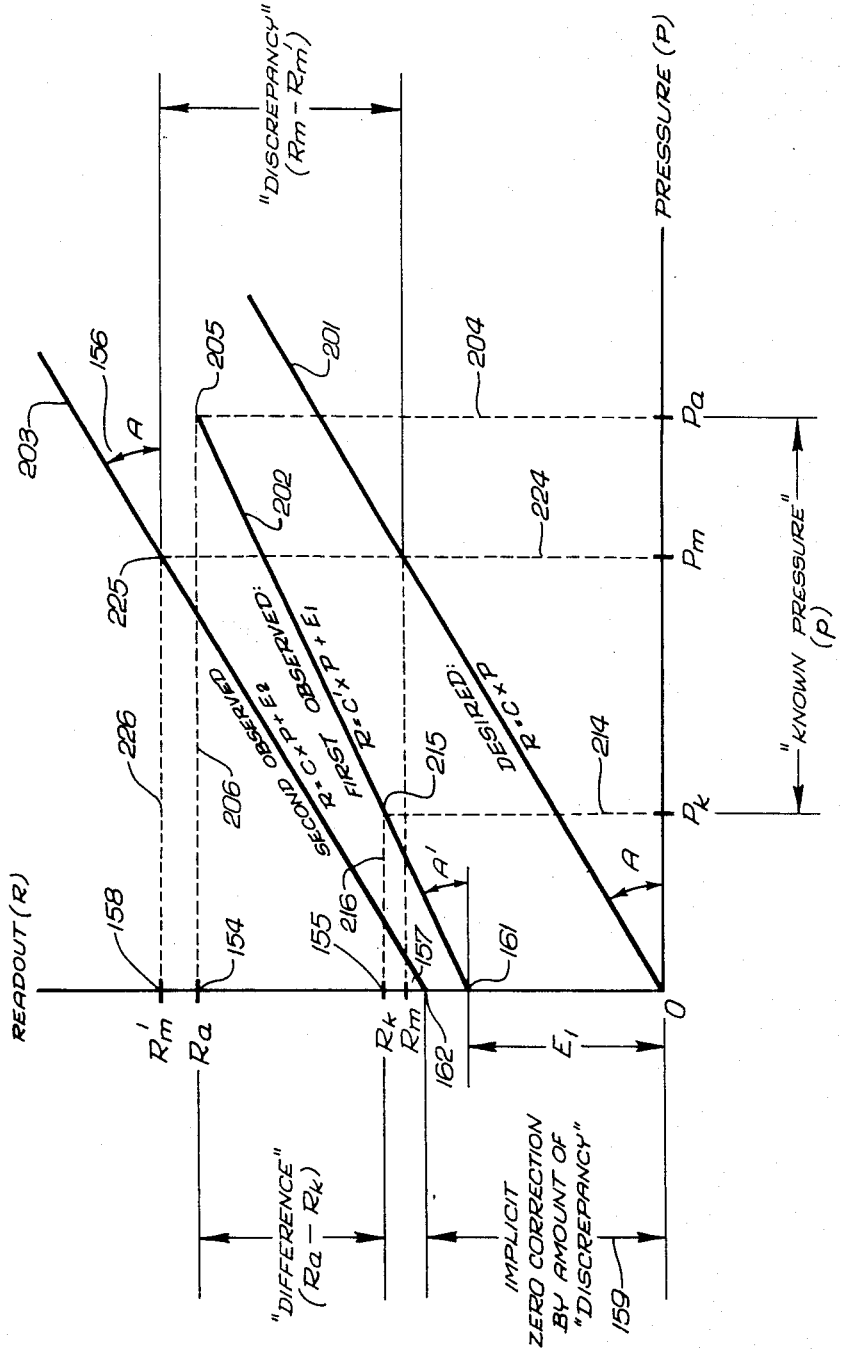

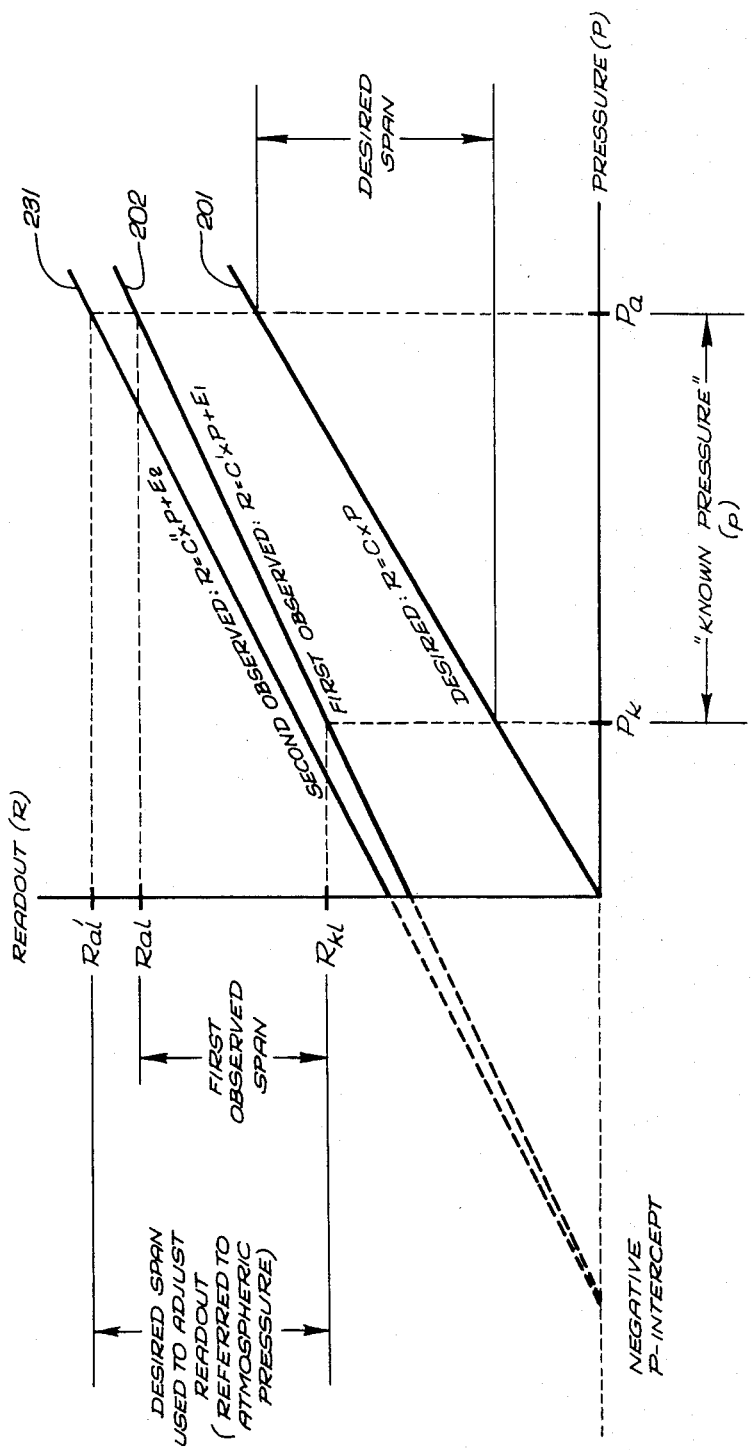

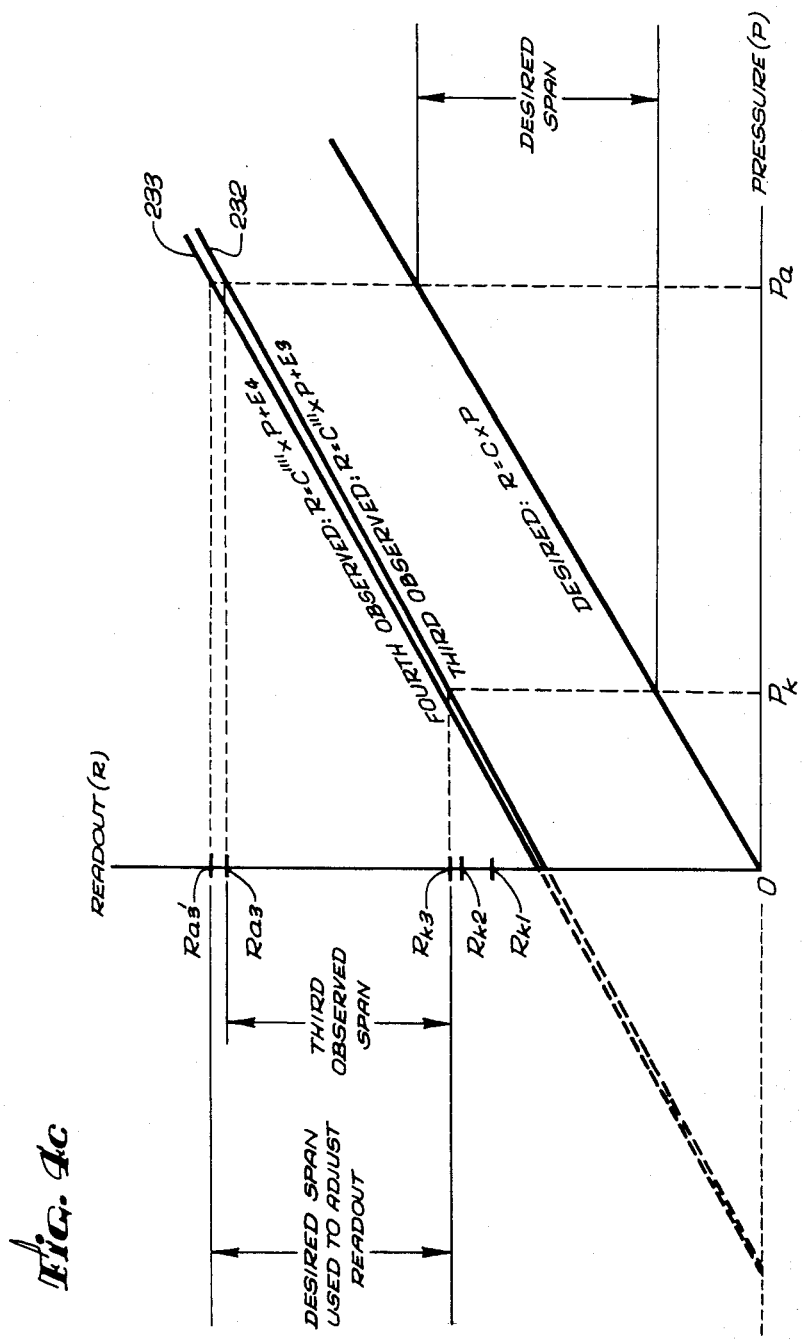

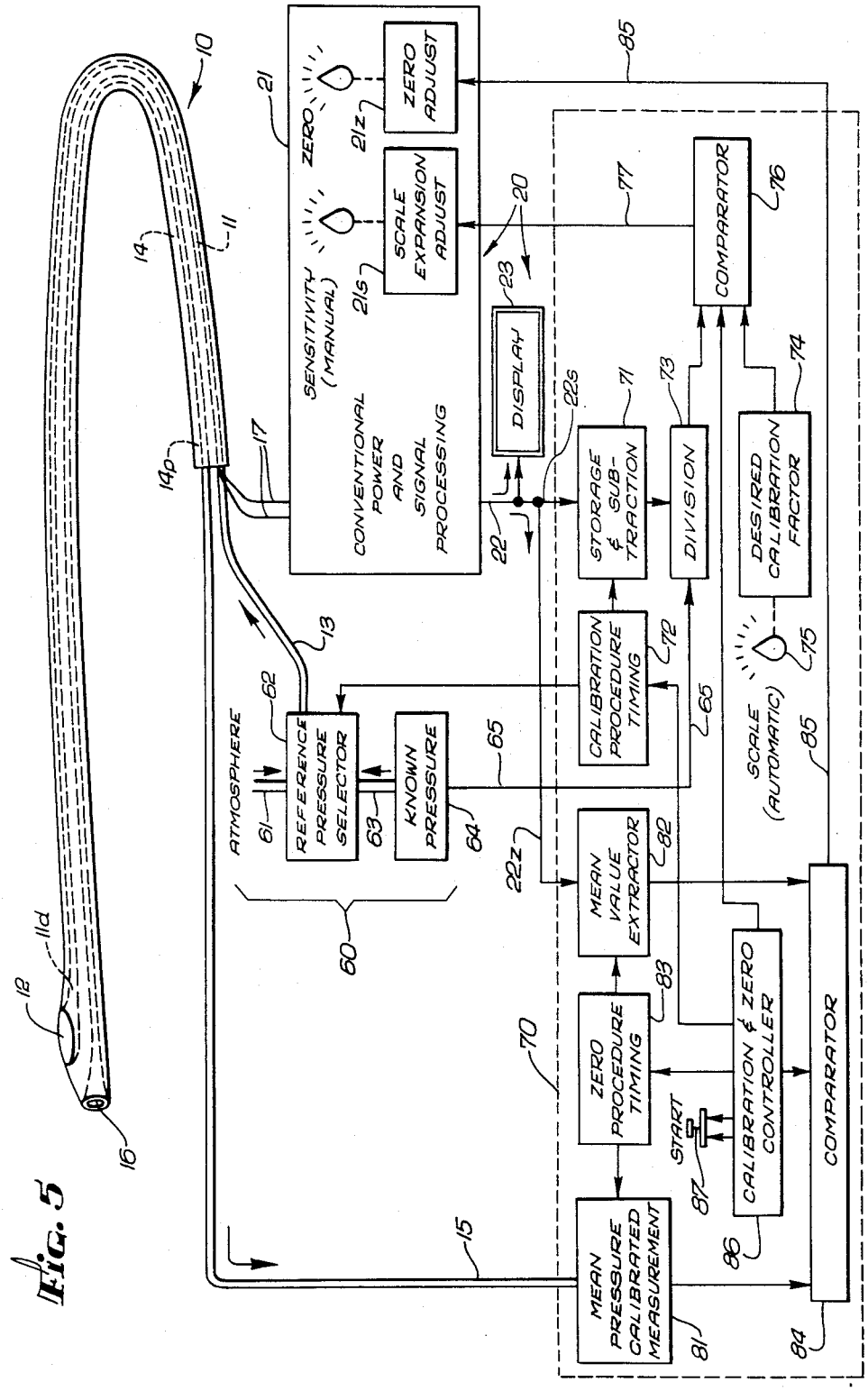

METHOD AND APPARATUS FOR "ZEROING" AND CALIBRATING A CATHETER-TIP GAUGE-PRESSURE TRANSDUCER

BACKGROUND

1. Field of the Invention

This invention relates generally to catheter-tip pressure transducers, and more particularly to methods and apparatus for "zeroing" and calibrating medical catheter-tip gauge-pressure transducers.

2. Prior Art

Catheter-tip pressure transducers are sometimes used, because of the dynamic error encountered in external measurement of intravascular pressure through a long narrow catheter. (By "dynamic error" I refer to poor fidelity in the tracking of rapid pressure variations—such as are found in cardiovascular pressure measurements.)

Heretofore, however, surgical workers and researchers alike have known no effective technique or apparatus for "zeroing" and calibrating ordinary catheter-tip pressure transducers in vivo—that is, while the transducer is in place within a patient's body. (By "calibrating" I mean adjusting the calibration factor or "sensitivity" of an instrumentation package that includes a pressure transducer and a display apparatus.)

In the medical field the usual technique of zeroing and calibrating a pressure transducer involves substituting a zero pressure, and then a known reference pressure, at the measurement side of the transducer, and adjusting the display apparatus to read as it should for the zero and known reference pressures respectively. Zeroing is performed before calibrating, since the calibration process then requires only matching of the readout at one point, near full-scale; and since interactions of the zero and readout mechanisms are minimized by proceeding in this order.

Such techniques normally are impermissible in vivo, because the measurement side is applied to the patient's blood stream or is within some other conduit or vessel of the body. Changing the pressure within the patient's body is not practical for ordinary catheter usage.

The words "normally" and "ordinary" are used in the preceding paragraph because one system has been put forward that is intended to permit in vivo calibration by, in effect, changing the pressure on the measurement side of the transducer. This system, disclosed in U.S. Pat. No. 3,703,099 to William Rouse, involves a complicated special catheter structure that is not actually available.

Zeroing and calibration techniques immediately prior to catheterization are generally impractical due to instrument-sterilization requirements—and in any case are inadequate for the duration of application of the pressure-measurement system.

Consequently, medical personnel have been limited to checking the transducer zero and calibration after completion of the particular procedure calling for catheterization. Such a sequence of events has several drawbacks. First, medical judgments and even irreversible decisions are sometimes rendered on the basis of the pressure indications made during the particular procedure.

Moreover, even judgments rendered after the medical procedure and the zeroing and calibration are all complete may be misleading. There is a possibility of significant drift in zero or calibration, or both, between the time of the intravascular measurements and the time of subsequent zeroing and calibration. Cather-tip pressure transducers are commonly expected to exhibit significant drift of both zero and sensitivity with time, temperature and use.

Furthermore, catheter pressure transducers commonly exhibit nonlinearity and hysteresis. When these exceed acceptable levels, as sometimes happens, post-measurement zeroing and calibration are inadequate to rescue the intravascular measurements or any decisions made in reliance upon them.

Checking the nonlinearity and hysteresis, however, in effect requires making multiple measurements of calibration. As already explained, in the prior art even one such measurement has been impractical in vivo, except by the employment of a complicated, unavailable special catheter structure.

It will be helpful to review briefly the configuration of equipment used in the prior art. Typically the electrical leads of a catheter-tip transducer either run through a lumen of the catheter, or are embedded in a solid part of the catheter.

It is gauge pressure that is measured with catheter-tip transducers; consequently the catheter has a lumen that conducts atmospheric pressure to the reference side of the transducer—i.e., to the "back" of the transducer diaphragm. This lumen may be used to carry the electrical leads too (if they run through a lumen), or this lumen may be one that is provided in addition to any lumen used for the transducer leads. To avoid contamination the opening of this lumen that is connected to the reference side of the transducer is typically buried inside the connector (with free access to atmospheric pressure) of the electrical cable that carries the transducer excitation and signals between the catheter and the instrumentation.

(In this field of catheters the terms "proximal" and "distal" are customarily referred to the operator, rather than to the patient's body. Hence the open end of the atmospheric-pressure lumen that is outside the patient's body and most proximal to the operator and the electronics is known as the "proximal" end. The same convention is used for other features of the catheter.)

Such a catheter often has at least one other lumen, which in this document will be called an "auxiliary" lumen. Such an auxiliary lumen is used in the prior art to administer medication or withdraw blood samples at or near the pressure-measurement site.

Based upon the foregoing discussion it may be understood that prior art in the field of catheter-tip transducers fails to provide reliable and safe measurement of cardiovascular and other rapidly varying pressures using ordinary catheter-tip transducers.

SUMMARY OF THE INVENTION

This invention rests upon the fact that while a linear system containing mass and compliance elements is generally oscillatory, and thus responds differently to different driving-force frequencies (i.e., signal frequencies) the response to the "d.c." portion of a driving force (i.e., to the mean value of a signal) is true and linear and unaffected by any resonances.

Thus, while an external pressure transducer of any type is not able to faithfully follow the dynamic pressure fluctuations occurring at the end of a long, narrow tube, it may accurately measure the mean value of that pressure. The "averaging" (filtering) may be done hydraulically, by including a resistance in the long narrow tube, or electronically, upon the transducer's output signal.

By increasing the reference pressure of the catheter-tip transducer (which is normally ambient atmospheric) by a known amount $\Delta P_R$, which is of course measurable outside the patient, the "apparent" pressure in the patient's blood vessel as seen by the catheter-tip transducer is reduced by the observable decrement $\Delta T$. The change in the mean output of the catheter-tip transducer then represents the calibration factor $$\Delta V/\Delta P_r = \Delta V/\Delta T.$$

My invention provides both methods and apparatus for calibrating, and also for zeroing, a medical catheter-tip gauge-pressure transducer system. In principle the calibration method and apparatus may be used without the zeroing method or apparatus; however, the zeroing method requires prior performance of some reliable calibration method.

When my invention is used with such a transducer system, the system has a pressure-sensitive diaphragm with a measurement side that is normally exposed to pressures to be determined, and a reference side that is normally exposed to atmospheric pressure. Such a system also has a display apparatus which is responsive to the diaphragm to provide an indication of the pressure to be determined relative to atmospheric pressure. The display apparatus has adjustable scale expansion, and the display apparatus also has an adjustable "zero" or "offset."

The calibration method in a preferred embodiment includes these steps:

(a) noting the pressure indication produced by the display apparatus while the transducer is in position within a patient's body and the reference side of the transducer is exposed to atmospheric pressure;

(b) then substituting a known pressure for atmospheric pressure at the reference side of the diaphragm to produce a new pressure indication;

(c) then using the noted pressure indication of step (a), the known pressure of step (b), and the new pressure indication of step (b) to adjust the display apparatus scale expansion to provide a desired calibration factor; and (d) then restoring atmospheric pressure at the reference side of the diaphragm.

As will be seen, this procedure for calibrating the catheter-tip transducer system—and particularly step (c)—is amenable to several variations within the scope of my invention.

Now turning to the zeroing procedure, a preferred embodiment of my invention consists of these steps:

(a) first calibrating the display apparatus;

(b) after step (a), independently measuring the mean pressure substantially at such location;

(c) after step (a), determining a mean value of the display-apparatus indication; and (d) using the mean value of the display-apparatus indication and the independently measured mean pressure to adjust the display-apparatus zero control in such a way as to substantially eliminate discrepancy between the mean value and the mean pressure.

This zeroing procedure too, and particularly step (d), will be seen to have certain variants within the scope of my invention. Step (a) is best performed by using my previously presented procedure for calibrating the transducer.

Now referring to a preferred embodiment of the apparatus of my invention, it is a measuring apparatus for determining gauge pressure at locations within a patient's body. This apparatus includes electronic circuitry for providing an indication of the gauge pressure. The circuitry has adjustable scale expansion and zero.

The preferred-embodiment apparatus also includes a catheter. The catheter is adapted to extend to the measurement locations from outside the patient's body, and it has these features: (1) a first portion which, when the catheter is in use, is within the patient's body and distal with respect to the circuitry, (2) a second portion which, when the catheter is in use, is outside such patient's body and proximal with respect to the circuitry, and (3) at least two lumens defined within the catheter and communicating between its proximal and distal portions.

The apparatus of my preferred embodiment also includes a pressure transducer in the first portion of the catheter. The circuitry is responsive to this transducer.

The pressure transducer has a measurement side that is exposed to the pressure outside the catheter, and has a reference side that is exposed to the proximal end of a first one of the two lumens. This first one of the two lumens is sealed at its distal end against the pressure outside the catheter. The other one of the two lumens is exposed at its distal end to the pressure outside the catheter.

My preferred-embodiment apparatus also includes some means for selectively connecting the first one of the two lumens, in its proximal portion, for communication with either: (1) atmospheric pressure, for measurement of such gauge pressure within such patient's body, or (2) a known pressure source, to facilitate calibrating the adjustable scale expansion of the apparatus.

All of the foregoing operational principles and advantages of the invention will be more fully appreciated upon consideration of the following detailed description, with reference to the appended drawings, of which:

BRIEF DESCRIPTION OF THE DRAWINGS

FIG. 1 is a highly schematic drawing of a catheter-tip transducer system which is usable with a preferred embodiment of the methods of my invention.

FIG. 2 is a diagram of a preferred embodiment of the methods of my invention.

FIG. 3 is a graph showing the relationships between display readout and actual pressure, when calibration and zero are set incorrectly and when they are set correctly, and the way in which a preferred embodiment of the methods of my invention produces correct calibration and zero.

FIGS. 4a through 4c are a series of similar graphs for another embodiment of my method invention, but showing only how this embodiment produces correct calibration.

FIG. 5 is a functional block diagram of a preferred embodiment of the apparatus of my invention.

DETAILED DESCRIPTION OF PREFERRED EMBODIMENTS

Figure 4B:
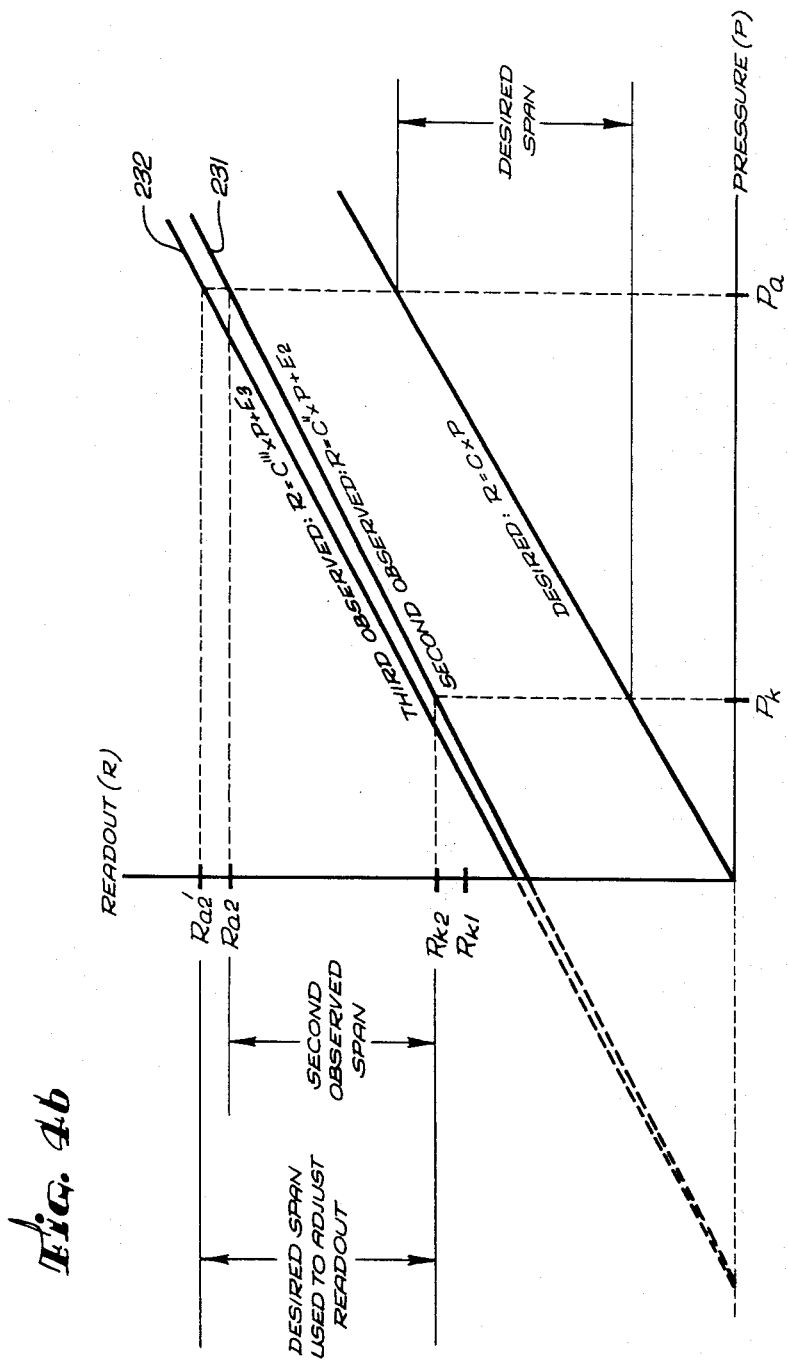

A catheter-tip pressure transducer system, as shown in FIG. 1, exists in the context of a catheter 10. The transducer system includes a pressure-responsive diaphragm having a "front" or "pressure-measuring" side 12; and a transducer element (not illustrated) at the "back" of the diaphragm, which provides an electrical signal related to displacement of the diaphragm 12.

The system also includes a lumen or conduit 11 running through the catheter 10 for conducting air at substantially atmospheric pressure from the open proximal end 11p of the lumen 11 to the "back" or "reference pressure" side of the diaphragm near the distal end 11d of the lumen 11. This lumen 11 is necessary to make the transducer system read gauge pressure—the pressure relative to atmospheric pressure.

The transducer system also includes electrical leads 17 that run between the transducer element and an external electronics package 20. The latter typically includes a power and signal-processing unit 21, with output leads 22 to a display device 23, which often includes a recorder. The electrical leads 17 may run through the lumen 11 or may be embedded in the solid wall or center of the catheter 10.

A cable sheath is typically provided for protection of the leads 17 between the proximal end of the catheter and the electronics package 20, and the proximal end 11p of the atmospheric reference lumen 11 is sometimes buried inside this cable sheath to prevent contamination of the lumen 11. In such a configuration the proximal end 11p of the lumen 11 is generally inaccessible, which in the prior art is desirable or at least unobjectionable. For purposes of my invention, however, the proximal end 11p of the lumen 11 should be brought out to a separate fitting or termination 13.

The catheter-tip transducer system also often has an auxiliary lumen 14 which runs through the catheter from a port 16, defined at the distal end 14d of the auxiliary lumen 14, to an external fitting 15, which terminates the proximal end 14p of the auxiliary lumen 14. The auxiliary lumen is sometimes provided in the prior art for the purpose of administering medication to the catheterized patient or withdrawing fluid samples from within the patient's body. In my invention the auxiliary lumen 14 is used for obtaining a measurement of the mean pressure within the patient's body at a point near the diaphragm 12.

As shown in FIG. 2, the zeroing and calibration procedures of a preferred embodiment of my invention follow the preliminary step of catheter emplacement 51. This is important because it means that both procedures are carried out in vivo—i.e., while the catheter 10 is in position within the patient's body—and in particular with the diaphragm 12 exposed to the very environment in which it will be used to make pressure measurements. Consequently the zeroing and calibration procedures are subject to the barest minimum of drift with time or temperature. In fact these procedures may be repeated virtually as often as desired during the course of the pressure measurements, and the amount of drift assessed as well as cancelled.

In accordance with my invention a calibration procedure 53 is the first step in the zeroing procedure 52. This sequence is itself at least unusual, since as previously mentioned the usual procedure for adjusting measuring instruments is to begin with zeroing and then proceed to calibration. This more usual or customary procedure has various justifications, but in any event it is extremely pervasive, showing that the prior art teaches away from my invention.

It will be understood that in principle any reliable calibration procedure 53 may be used as the first step in my zeroing procedure 52, but the calibration procedure of my invention (as outlined within the calibration-procedure block 53) is particularly effective and useful.

My calibration procedure, as previously stated, consists of three basic steps: noting 54 the pressure indication referred to atmospheric pressure, substituting 55 a known reference pressure for atmospheric pressure to produce a new indication, and adjusting 56 the scale expansion to obtain a desired calibration factor. The last of these steps is performed using the noted and new indications and the known pressure.

The substitution step 55 requires access to the proximal end 11p (FIG. 1) of the reference-pressure lumen 11. This is the reason for bringing that proximal end 11p to an accessible fitting 13 rather than leaving the proximal end 11p within the electronics-cable jacketing as in typical prior art.

As shown within the adjusting-step block 56 of FIG. 2, I prefer to perform the adjusting step by using four substeps. The first of these is determining of the actual calibration factor for the system initially. The second is determination of the "error" in this actual calibration. (In this last sentence I have used quotation marks because the selection of calibration factor is in a certain sense arbitrary. As a practical matter, however, there is some calibration factor that is desired, and the difference between the two is an "error" in this practical sense.)

The third preferred substep for the adjusting step 56 is to adjust the expansion to eliminate the error, and the fourth substep is to restore the atmospheric-pressure reference.

Now as to implementation of these four preferred substeps, I prefer to determine the actual calibration, as shown in FIG. 2, by first subtracting the new indication from the noted indication and then dividing the resulting difference by the known pressure. The quotient is the actual calibration factor for the particular span of pressures and indication values involved. To the extent that the system is linear over the pressure range of interest, this same quotient is an actual calibration factor for all pressures and indication values of interest. The possibility of significant nonlinearity will be discussed further below.

Turning to the second preferred substep, I prefer to determine the "error" in actual calibration as a percentage. In other words, the quotient just obtained is subtracted from the desired calibration factor, the resulting difference is divided by the desired calibration factor, and the resulting quotient is multiplied by one hundred. As will be apparent to those skilled in the art, equivalently the error can be determined as a fraction instead, merely by omitting the last multiplication.

The third preferred substep involves adjusting the scale expansion to eliminate the observed percentage (or fractional) error. The substeps and their details as illustrated in FIG. 2 are set forth under the assumption that the scale-expansion or sensitivity control is itself "calibrated"—that is to say, has a pointer and markings associated with it, or has some associated display—that shows the scale expansion or sensitivity value in use at the moment of observation.

The display or control does not read accurately with respect to an absolute standard (if it did, no calibration procedure would be required), but it is typically approximately linear in scale expansion or sensitivity, and this is all that is required. (An alternative procedure for use if the sensitivity control is not calibrated will be discussed below.) Care must be taken to distinguish between the use of the word "calibrated" in regard to the calibration of the scale-expansion control or display, and the use of the same word in regard to the sensitivity or scale expansion of the overall transducer system. The first of these is merely a nominal or roughly approximate indication of the second.

With this assumption in mind, the adjustment substep is performed by noting the scale expansion indicated by the display or control, multiplying this expansion by the percentage error to obtain a correction increment, and resetting the control by the amount of the increment.

In multiplying the expansion by the percentage error it is of course necessary to divide by one hundred; if a fractional error is used the division by one hundred is not necessary. In resetting the control by the amount of the increment, it is necessary to refer to the calibrations on the control—or to the display—to determine the setting before the adjustment, the desired setting to be obtained after the adjustment, and the progress toward that desired setting.

Moreover it is also important to move the control (or display indication) in the correct direction, as well as by the correct amount. The direction is implied by the polarity of the percentage error, which is carried over to the resulting correction increment in the multiplication used to find that increment.

Once calibration 53 is complete, the zeroing procedure 52 is completed by three additional steps: independently measuring 57 the mean pressure, determining 58 the mean value of the display indication, and adjusting 59 the zero point of the system to eliminate any discrepancy between the mean pressure and mean value.

The mean-pressure measuring step 57 is performed by detecting and measuring the mean pressure in the proximal end 14p of the auxiliary lumen 14 (FIG. 1). As previously mentioned such measurements are inadequate for determination of the dynamic behavior of intravascular pressures, due to the poor dynamic performance of a long slender conduit as a pneumatic transmission line. For determination of mean pressure, however, the auxiliary lumen 14 is entirely adequate: in a linear system no "rectification" or conversion of a.c. to d.c. occurs, and therefore the constant (or d. c.) component is preserved regardless of any resonances that may be present in the system.

If the pressure being measured 57 varies periodically, or very nearly so, then both the mean pressure and mean indication value are ideally measured 57, 58 over a time interval equal to an integral number of fluctuation periods. This is generally the case with blood-pressure measurements. Timing is best arranged by use of automatic equipment, though a highly skilled operator will be able to start and stop the measurements accurately enough for good results.

Both measurements 57 and 58 may be started and stopped in common (e.g., by a common switch) if desired. Due to phase differences between the two measurement signals, however, better accuracy will be obtained by starting and stopping the two measurements at corresponding points in the waveforms of the two measurement signals as monitored individually.

If the fluctuations are not essentially periodic, the two means should both be measured 57, 58 over a time interval that is relatively long in comparison with the principal fluctuations of interest. In this case, timing requirements are not at all difficult to satisfy manually.

In regard to the final step 59 of the zeroing procedure, FIG. 2 is drawn under the assumption that the zero control is itself calibrated—in units of pressure. Thus the final zero-adjusting step 59 is performed by subtracting the mean pressure from the mean value, and using the resulting difference to adjust the zero point. In particular, the zero point is adusted upwardly or downwardly by the amount of the percentage difference, and in opposition to the sense of the difference.

As in the case of an uncalibrated scale-expansion control, iterative substeps may be used to carry out the final step 59 if the zero control is not itself calibrated.

Most medical technicians—that is to say, most persons skilled in the art of surgical, diagnostic, and research procedures—should be able to practice my invention by a rote following of the procedures that are described in FIG. 2 and in the above paragraphs. For those who wish a deeper comprehension, the physical results of the preferred embodiment of FIG. 2 may be understood from FIG. 3 and the discussion that follows.

FIGS. 3 through 4c and the corresponding discussion are intended to be understood by anyone who has a good working understanding of algebra; hence, based on careful study of FIGS. 1 through 4c and the accompanying discussion, most skilled medical technicians will be able to comprehend the methods of my invention fully as well as to practice them.

FIG. 3, like the details of FIG. 2, applies only when the scale-expansion and zero controls of the system are themselves both calibrated. FIG. 3 shows the relationship between the indication or readout R of the system and the actual pressure P applied to the diaphragm face 12 and auxiliary-lumen port 16 (FIG. 1). Thus pressure values are plotted along the abscissa or P axis, and readout values along the ordinate or R axis.

Ideally the readout R and pressure P are related by a straight line 201 on the graph. This line 201 represents the relationship $R = C \times P$; thus the line passes through the origin or zero point at bottom left. The meaning of these symbolisms is simply that the readout is directly proportional to the pressure, without any zero error.

Further, the symbol C represents some desired calibration factor, in units of readout per unit of pressure. On the graph, C is also the slope of the line 201, and is equal to the trigonometric tangent of the angle A which the line 201 makes with the abscissa or P axis. Hence the angle A is directly related to the calibration factor C.

By comparison, the line 202 represents the state of the instrumentation system when the procedures of FIG. 2 begin. For the moment adequate linearity is assumed; consequently line 202 is presented as a straight line. This line 202 represents the relationship $R = C' \times P + E_1$, in which the value C' is some incorrect calibration factor or slope, not equal to the desired factor C. Correspondingly the angle A' between the line 202 and the abscissa is not equal to the desired angle A. Furthermore there is a zero offset or error $E_1$ which is added to all readout values; this error $E_1$ appears on the graph as the so-called "R intercept" 161 of the line 202—the point where the line 202 crosses the R axis.

Shown on the P axis is the actual instantaneous gauge pressure $P_a$. This is the pressure within the patient's body referred to atmospheric pressure; hence the subscript "a". The corresponding readout is defined by following the vertical dashed line 204 from the gauge pressure $P_a$ to the intersection 205 with the "first observed" line 202, and from that intersection 205 following the horizontal dashed line 206 to its intersection 154 with the R axis. This geometric process represents the definition of a readout value $R_a$ by the apparatus, in its condition as characterized by the line 202.

My invention makes use of the fact that a known pressure p may be applied to the reference side of the diaphragm, through the lumen 11 (FIG. 1)—in place of atmospheric pressure. The result is to produce a pressure differential $P_k$ across the diaphragm that is referred to the known pressure rather than to atmospheric pressure; hence the subscript "k". This effective pressure $P_k$ on the diapgragm would be the gauge pressure if the atmospheric pressure were higher by the amount p.

The pressure on the measurement side 12 of the diaphragm is the same instantaneous pressure, within the patient's body, as before the substitution of reference pressures, but the pressure differential $P_k$ across the diaphragm is lower by the amount p. Consequently the difference $P_a - P_k$ between the two pressures across the diaphragm is exactly equal to the known pressure p. If the system were responding in accordance with the desired relationship 201, the difference between the readouts referred to atmospheric pressure and to the known pressure would be equal to the difference $P_a - P_k$ multiplied by the desired calibration factor C, or in other words $C \times (P_a - P_k)$, or $C \times p$.

Since, however, the system is instead responding in accordance with the incorrect relationship 202, the readout $R_a$ referred to atmospheric pressure will be $R_a = C' \times P_a + E_1$, and the readout $R_k$ referred to the known pressure will be $R_k = C' \times P_k + E_1$.

This latter readout value $R_k$ is related to the actual instantaneous pressure $P_k$ across the measurement diaphragm when the known pressure is applied to the reference side. This pressure $P_k$ is shown on the P axis. The corresponding readout $R_k$ is defined by following the vertical dashed line 214 from the differential pressure $P_k$ to the intersection 215 with the "first observed" line 202, and from that intersection 215 following the horizontal dashed line 216 to its intersection 155 with the R axis. This geometric process represents the definition of the readout value $R_k$ by the apparatus, in its condition as characterized by the line 202.

The difference between the two readouts is therefore $R_a - R_k = C' \times (P_a - P_k)$, since the $E_1$ values in the expressions for the two readouts will cancel in subtraction. Since the expression $P_a - P_k$ is equal to the known pressure p, the difference between readouts can also be expressed as $R_a - R_k = C' \times p$.

Now comparing this observed difference with the ideal difference presented in the preceding paragraph, one sees that the two values differ by the factor $C/C'$. To correct the readout relationship to reflect the desired calibration factor, it will be necessary to change $C'$ by the percentage or fractional amount $(C - C')/C'$.

In this last expression the value C is given: it is the desired calibration factor. The value $C'$, however, which as will be recalled is the actual initial calibration factor, must be measured. From the expression given above for the difference between readouts, $R_a - R_k = C' \times p$, the value $C'$ can be found as $C' = (R_a - R_k)/p$. This is the observed difference between the two readouts, divided by the known pressure p.

In other words, the actual calibration factor $C'$ is equal to the difference between the originally noted indication $R_a$ and the new indication $R_k$ seen with the known pressure applied to the lumen 11, divided by the magnitude of that known pressure p. (Once the new indication has been noted, atmospheric pressure can be restored at the reference side of the diaphragm.)

When the calibration factor $C'$ has been corrected as previously explained to equal the desired calibration factor C, the system will perform as represented by the "second observed" line 203. Here the slope is C rather than $C'$, and the angle of the line 203 to the abscissa is now A rather than $A'$. In short, the line 203 is parallel to the desired line 201; however, it is still offset vertically, as can be seen, for example, by the fact that the line 203 intercepts the R axis at a point 162 well above the origin, while the desired line 201 passes through the origin. (It should also be noted that the line 203 intercepts the R axis at a different point 162 than the intercept 161 of the "first observed" line 202.)

The pressure within the patient's body cannot be adjusted to zero for the purpose of adjusting the zero point, but the mean gauge pressure $P_m$ can be independently measured through the auxiliary lumen 14. If the desired system condition 201 were in effect, the readout would be $R_m = C \times P_m$. The desired calibration factor C is known, and the mean gauge pressure $P_m$ independently measured; therefore the desired readout $R_m$ can be calculated.

Since the system is instead in the "second observed" condition 203, however, the actual readout $R_m'$ is defined by following the vertical dashed line 224 upward from the mean pressure $P_m$ to the intersection 225 with the condition line 203, and then following the horizontal dashed line 226 leftward from that intersection 225 to the intersection 158 with the R axis.

The discrepancy $R_m - R_m'$ between the correct readout and the actual readout is shown at the upper right in FIG. 3. When the calibrated zero control is adjusted "downward" by the amount of this discrepancy (step 59 in FIG. 2), the observed readout $R_m'$ for the gauge pressure $P_m$ is adjusted into coincidence with the desired readout $R_m$ for that pressure. Further, within the tolerances of the procedure, the entire actual-condition line characterizing the system is thereby shifted from the position 203 downward by the amount of the discrepancy into coincidence with the desired condition line 201. This shift is symbolized in FIG. 3, near the lower left-hand corner of the drawing, by the "implicit zero correction" 159.

In addition to zero and sensitivity drift with time and temperature, as earlier mentioned, cathether-tip pressure transducer systems are subject to nonlinearity and hysteresis. If present to an advanced degree in a given production unit, these behaviors render the unit useless. My invention provides a means of measuring these characteristics immediately upon emplacement of the catheter, before any reliance is placed upon the transducer system.

All that is required to obtain linearity information is to perform the procedures already described, and then to perform steps 54, 55 and the first substep of step 56 for each one of several known pressures p, while keeping track of the calibration factors $C'$ found for each known pressure p. From this information a curve or table of sensitivity $C'$ vs. pressure $P_k = P_a - p$ is readily developed in a very short time. Such a curve or table is readily used by a skilled worker to determine whether the system is adequately linear.

If nonlinearity is severe, the catheter and transducer can be replaced and the testing procedure repeated before the medical procedure begins. Alternatively, in constrained circumstances, even if the system is rather nonlinear the curve or table can be used to generate a calibration curve or table, for use in interpreting the readout values.

All that is required to obtain hysteresis information is to perform the procedures already described, and then to perform steps 54, 55 and the first substep of step 56 while adjusting the known pressure source toward the known pressure p from different directions and by different amounts. If different values of $R_k$ result for identical values of known pressure p, the operator can assess the severity of the hysteresis to determine whether the transducer must be replaced or is adequate.

If the calibration and zero controls are not themselves calibrated, then the details of the substeps within the adjustment steps 56 and 59 in FIG. 2 cannot be performed. It is still possible, however, to calibrate and zero the system using steps 54, 55, 57 and 58, and using substitute substeps for the adjustment steps 56 and 59.

In particular, for the calibration procedure 53, the scale-expansion adjustment step 56 may be performed by these substeps: (1) determining the pressure-indication value that would be consistent with the noted pressure indication of step 54, the known pressure indication of step 55, and the desired calibration factor; then (2) restoring atmospheric pressure at the reference side of the diaphragm; next (3) adjusting the scale expansion to move the actual pressure indication to that determined value; and finally (4) iterating the sequence of steps 54 and 55 through the adjustment in substep (3) of step 56—until no significant adjustment is needed in substep (3).

The value-determining substep (1) described in the above paragraph preferably consists of finding the product of the known pressure of step 55 and the desired calibration factor, then adding that product to the new pressure indication of step 55.

FIGS. 4a through 4c illustrate how this procedure affects the system. The desired line and first observed line are the same as in FIG. 3, but in this situation it is desirable to begin step 56 by computing the "desired span" of readout values that corresponds to the known pressure p and the desired calibration factor C. The desired span is equal to the product $C \times p$.

The "first observed span," however, will be a different value which can be learned by subtracting the first observed readouts $R_{a1}$ and $R_{k1}$. This subtraction step is not really necessary, however, since it is more productive to add the desired span $C \times p$ to the first observed readout $R_{k1}$ seen with the pressure referred to the known standard pressure $P_k$—i. e., to the "new" pressure indication. This sum represents a first approximation $R_{a1}'$ to a readout referred to atmospheric pressure that is consistent with the readout $R_{k1}$ referred to the known pressure.

Now if—as illustrated in FIG. 4a—the first observed readout $R_{a1}$ differs from this sum $R_{a1}'$, then the calibration control is simply adjusted to force the observed readout to the sum value $R_{a1}'$. The result is a new "second observed" condition line 231, which typically can be represented as another line passing through the same negative P-intercept point as the "first observed" line 202. As will be noted, the second observed line 231 is more nearly, but not exactly, parallel with the desired line 201.

When the foregoing procedure is iterated once, as shown in FIG. 4b, the iteration yields a second observed readout $R_{k2}$ referred to known pressure, and a second observed readout $R_{a2}$ referred to atmospheric pressure. (It will be noted that the second observed readout $R_{k2}$ referred to known pressure is significantly shifted relative to the first such observed readout $R_{k1}$.) To the former $R_{k2}$ is added the same desired span $C \times p$ to obtain a second approximation to a consistent readout, as before; and then the second atmospheric-pressure-referred readout $R_{a2}$ is compared with the second-approximation sum $R_{k2} + C \times p$.

Once again, if the readout $R_{a2}$ differs significantly from the second-approximation sum $R_{k2} + C \times p$, the calibration control is adjusted to force the readout to the sum value. The result is a third observed line 232 that is even more nearly, but still not exactly, parallel with the desired line 201.

The process may then be repeated again, with the results illustrated in FIG. 4c. Here the third observed readout $R_{k3}$ referred to the known pressure is again significantly shifted relative to the second such observed readout—but as shown in FIG. 4c, this shift is by a smaller amount than the shift between the first and second readouts. The desired span $C \times p$ is added to the third observed readout $R_{k3}$, producing a third-approximation sum $R_{a3}'$. This sum differs only slightly from the observed readout referred to atmospheric, $R_{a3}$, but the calibration control can again be adjusted to force the readout to the sum value $R_{a3}'$.

The result is a "fourth observed" line 233 which is even more nearly, but still not exactly, parallel with the desired line 201. If desired the procedure may be iterated further, until no significant adjustment is required. In successive iterations the observed readouts referred to the known pressure will differ by progressively smaller amounts, and the corrections will be progressively smaller. When the iteration is ended, the condition of the system will be as illustrated in FIG. 3 for line 203.

After that point has been reached, if the system has a calibrated zero control the procedure can revert to that shown in FIG. 2 in block 59, and the results of that procedure will be as shown in FIG. 3 and already discussed.

If the system has no calibrated zero control, however, then the zero-adjusting step 59 may be performed by these substeps: (1) adjusting the adjustable zero of the display apparatus to move the mean value of the display-apparatus indication of step 58 toward the independently measured mean pressure of step 57; and (2) iterating the sequence of steps 57 and 58 through substep (1) of step 59, until no significant adjustment is required at substep (1).

The amount of adjustment in substep (1) should be determined by watching the readout, and displacing the readout by the amount of the "discrepancy" between mean value and mean pressure. No more than a very small number of iterations should be required at substep (2).

The foregoing procedures may be carried out manually or automatically. FIG. 5 shows certain pneumatic hardware 60 and an electronics package 70 that are essentially automatic.

Partial automation may be achieved by building equipment with only some of the features illustrated in FIG. 5 and described below. For example, a very considerable improvement in convenience can be effected simply by providing the pneumatic hardware 60. Many other possible subsets of the features illustrated in FIG. 5 will occur to a person skilled in the art, and it will be apparent to such a person that corresponding costs and benefits will accrue to the various selections of such subsets.

The pneumatic hardware 60 includes a reference-pressure selector stopcock 62 connected to the proximal end 11p of the lumen 11. One leg of the stopcock is connected as through a conduit 61 to vent the lumen 11 to atmospheric pressure, and the other leg is connected as through another conduit 63 to a known pressure source 64. This hardware simplifies the chore of switching back and forth between measurements referred to atmospheric pressure and to known pressure.

As shown, the conventional circuitry 21 typically has an output 22 to a display device 23, and also has sensitivity and zero adjustment circuits 21s and 21z respectively, controlled manually. The electronic apparatus 70 of my invention taps control signals 22s and 22z out of the signal line 22 to the display device, for use in sensitivity and zero adjustment respectively; and also taps control signals 77 and 85 back into the conventional circuitry 21 for automatic operation of the scale and zero adjust circuits 21s and 21z respectively.

The electronics 70 should include a manual control 75, or a keyboard, or other equivalent means for entering the desired calibration factor (C in FIGS. 3 through 4c) to a block 74 that stores this information.

The display signal entering the electronics 70 at 22s is directed to a storage and subtraction block 71. This block is operated by a calibration-procedure timing block 72, which also automatically operates the reference-pressure selector stopcock 62. The storage and subtraction block 71 is keyed in synchronism with the selector stopcock 62, to identify and store readout values $R_a$ and $R_k$ (FIG. 3) as they are generated, and to direct them to an arithmetic-division block 73.

The division block also receives a signal at 65 from the known pressure source 64, automatically conveying the instantaneous value (p in FIG. 3) of the known pressure for use in the division block 73. As will be apparent, there are various alternative ways for this information to be provided to the division block 73, including manual entry through a keyboard or manual control analogous to that at 75. The division block 73, in any event, divides the known pressure p into the difference $R_a - R_k$, and transmits the resulting quotient $(R_a - R_k)/p$ to a comparator 76. The comparator also receives the desired calibration factor C from the storage block 74, and if the quotient $(R_a - R_k)/p$ differs from the desired factor C the comparator 76 transmits a proportional adjustment signal at 77 to the scale-expansion adjustment circuit 21s in the conventional circuit.

The apparatus of my invention also includes connection of the auxiliary lumen via a conduit 15 to a mean-pressure calibrated measurement device 81 which may be associated with the electronics package 70 or may be elsewhere, as convenient. (The auxiliary lumen 14 may be disconnected from the measurement device 81 when the operators desire to use the lumen 14 for flow of medications into or samples out of the patient's body; or if preferred another auxiliary lumen may be provided for the latter purposes.) This measurement device 81 produces an electrical output signal accurately proportional to the mean pressure in the conduit 15, and hence in the lumen 11 and port 16. The output signal passes to a comparator 84.

The comparator 84 likewise receives a comparable signal from a mean-value extractor block 82, which derives the mean value of the display signal 22z. A zero-procedure timing block 83 controls both the pressure measurement device 81 and the mean-value extractor 82 so that both those blocks determine mean values of time intervals that are either (1) substantially an integral number of fluctuation cycles, if the pressure fluctuates periodically, or (2) long compared with the principal fluctuations of interest.

The comparator 84 uses the difference between the output signals from the mean-pressure and mean-value devices 81 and 82 to derive a zero-adjust correction signal 85 that suitably adjusts the zero-adjust circuit 21z in the conventional electronics 21.

Ideally the apparatus of my invention also has a calibration and zero controller 86, which may automatically key the calibration-procedure timing block 72 and the zero-procedure timing block 83, as well as the comparators 76 and 84, to perform the entire calibration and zeroing procedure when a start switch 87 is manually actuated. If preferred the controller 86 may instead be programmed to perform the entire procedure periodically, or whenever the display signals themselves are found to change in some defined fashion.

FIG. 5 is a functional diagram; hence most of the individual blocks and other features illustrated may be replaced by a programmed microprocessor having suitable input and output interfacing.

All of the foregoing discussion related to FIGS. 1 through 5, in combination with those drawings themselves, are believed to be sufficient to enable a reasonably skilled design engineer who is at the level of routine electromechanical design—which is to say, a person skilled in the art to which the apparatus embodiments of my invention pertain—to design and oversee the manufacture of an apparatus that will automatically perform the procedures described earlier.

It is to be understood that all of the foregoing detailed descriptions are by way of example only, and not to be taken as limiting the scope of my invention—which is expressed only in the appended claims.

I claim:

1. A method for first calibrating then zeroing a catherer-tip gauge-pressure transducer system having a pressure-sensitive diaphragm with a measurement side exposed to a pressure to be measured and a reference side normally exposed to atmospheric pressure, and haivng a display apparatus responsive to the diamphragm to provide an indication upon a calibratable scale of the pressure to be measured relative to atmospheric pressure said method comprising the steps of:
   (a) noting the pressure indicated by the display apparatus while the measurement side of the diaphragm is exposed to a pressure to be measured and the reference side of the diaphragm is exposed to atmospheric pressure; then
   (b) substituting a known pressure for atmospheric pressure at the reference side of the diaphragm to produce a new pressure indication; then
   (c) using the noted pressure indication of step (a), the known pressure of step (b), and the new pressure indication of step (b) calibrating the display apparatus scale in accordance with a calibration factor; then
   (d) while establishing a constant reference pressure at the measurement side of the diaphragm, determining a mean value of the calibrated display-apparatus indication plus independently measuring a pressure substantially at the location of the reference side of the diaphragm; then (e) calculating the difference between the independently measured pressure of step (d) and the calibrated display-apparatus indication of step (d); then (f) adjusting the zero of the display apparatus in such a way as to cancel the difference calculated in step (e); therein the display apparatus is calibrated, and is also zeroed for operation while the constant reference pressure is at the measurement side of the diaphragm.

2. The method of claim 1, wherein step (c) comprises the substeps of:

(c-1) determining the actual calibration factor represented by the noted pressure indication of step (a), the known pressure of step (b), and the new pressure indication of step (b);

(c-2) then determining the error in the actual calibration factor of substep (c-1), relative to the desired calibration factor of step (c);

(c-3) then adjusting the display-apparatus scale expansion to substantially eliminate the error; and (c-4) after step (c-1), restoring atmospheric pressure at the reference side of the diaphragm.

3. The method of claim 2, for use with a display apparatus that has a calibrated scale-expansion display or control, wherein:

substep (c-1) comprises finding the difference between the new pressure indication of step (b) and the noted pressure indication of step (a), and then dividing the difference by the known pressure of step (b) to yield the actual calibration factor; and substep (c-2) comprises calculating the percentage error in the actual calibration factor as found in substep (c-1) relative to the desired calibration factor of step (c); and substep (c-3) comprises noting the nominal scale expansion from the calibrated scale-expansion display or control, multiplying that nominal scale expansion by the percentage error found in substep (c-2) to obtain a scale-expansion correction increment, and resetting the calibrated scale-expansion display or control by an amount that is substantially equal to the correction increment.

4. The method of claim 1, wherein step (c) comprises the substeps of:

(c-1) determining the pressure-indication value that would be consistent with the noted pressure indication of step (a), the known pressure indication of step (b), and the desired calibration factor of step (c);

(c-2) after step (b), restoring atmospheric pressure at the reference side of the diaphragm; and (c-3) after steps (c-1) and (c-2), adjusting the scale expansion to move the actual pressure indication to that determined value.

5. The method of claim 4, wherein substep (c-1) comprises:

finding the product of the known pressure of step (b) and the desired calibration factor of step (c); and then adding that product to the new pressure indication of step (b).

6. The method of claim 5, further comprising:
iterating the sequence of step (a) through substep (c-3) until no adjustment is needed in substep (c-3).

7. The method of claim 4, further comprising:
iterating the sequence of step (a) through substep (c-3) until no adjustment is needed in substep (c-3).

8. A method for zeroing a medical catheter-tip pressure transducer system that has a pressure sensitive diaphragm, and that has a display apparatus which is responsive to provide an indication of the pressure to be determined at a location within a patient's body, such display apparatus having adjustable zero; said method comprising the steps of:

(a) first calibrating the display apparatus;

(b) after step (a), independently measuring the mean pressure substantially at such location;

(c) after step (a), determining a mean value of the display-apparatus indication; and (d) using the mean value of the display-apparatus indication and the independently measured means pressure to adjust the zero of the display apparatus in such a way as to substantially eliminate discrepancy between the mean value and the mean pressure.

9. The method of claim 8, for use with a display apparatus that has a calibrated zero control, wherein step (d) comprises the substeps of:

(d-1) determining the difference between the mean value and the mean pressure; and (d-2) adjusting the calibrated zero control by the difference determined in substep (d-1).

10. The method of claim 8, wherein step (d) comprises the substeps of:

(d-1) adjusting the adjustable zero of the display apparatus to move the mean value of the display-apparatus indication of step (c) toward the independently measured mean pressure of step (b); and (d-2) iterating the sequence of step (b) through substep (d-1) until no significant adjustment is required at substep (d-1).

11. The method of claim 8, wherein:
step (b) comprises detecting the pressure in the proximal end of an auxiliary tube whose distal end is within the patient's body near such location.

12. The method of claim 11, wherein:
the auxiliary tube is within the transducer catheter.

13. The method of claim 8, wherein:
in step (b), the mean pressure is measured over a time interval that is:
long compared with major fluctuations in such pressure, if such fluctuations are substantially nonperiodic, or
substantially equal to an integral number of periods, if such pressure fluctuates substantially periodically.

14. The method of claim 8, wherein:
in step (c), the mean value of the display-apparatus indication is determined over a time interval that is:
long compared with major fluctuations in the indication, if the fluctuations are substantially nonperiodic, or
substantially equal to an integral number of periods, if the indication fluctuates substantially periodically.

15. A method for first calibrating and then zeroing a medical catheter-tip gauge-pressure transducer system having a pressure-sensitive idaphragm with a measurement side exposed to a pressure to be measured and a reference side normally exposed to atmospheric pressure, and having display apparatus responsive to the diaphragm to provide an indication upon a calibratable and zero adjustable scale of the pressure to be measured, at a location within a patient's body, relative to atmospheric pressure, said method comprising the steps of:

(a) noting the pressure indicated by the display apparatus while the measurement side of the diaphragm is exposed to a pressure to be measured at the location within a patient's body and diaphragm is exposed to atmospheric pressure; then (b) temporarily substituting a known pressure for atmospheric pressure at the reference side of the diaphragm to produce a new pressure indication; then (c) using the noted pressure indication of step (a), the known pressure of step (b), and the new pressure indication of step (b) calibrating the display apparatus scale in accordance with a calibration factor; then (d) independently measuring the mean pressure substantially at such location; coincident with (e) determining a mean value of the calibrated display-apparatus indication while the reference side of the diaphragm is exposed to atmospheric pressure; and then (f) using the determined mean value of the calibrated display-apparatus indication and the independently measured mean pressure to adjust the zero of the display apparatus in such a way as to substantially eliminate discrepancy between the determined mean value and the independently measured mean pressure.

16. The method of claim 15, wherein:
step (d) comprises detecting the pressure in the proximal end of an auxiliary tube whose distal end is within the patient's body near such location.

17. The method of claim 16, wherein:
the auxiliary tube is within the transducer catheter.

18. The method of claim 15, wherein:
in step (d), the mean pressure is measured over a time interval that is:
long compared with major fluctuations in such pressure, if such fluctuations are substantially nonperiodic, or
substantially equal to an integral number of periods, if such pressure fluctuates substantially periodically.

19. The method of claim 15, wherein:
in step (e), the mean value of the display-apparatus indication is determined over a time interval that is:
long compared with major fluctuations in the indication, if the fluctuations are substantially nonperiodic, or
substantially equal to an integral number of periods, if the indication fluctuates substantially periodically.

20. Measuring apparatus for determining pressure at locations within a patient's body, said apparatus comprising:
electronic circuitry means, having calibratable scale expansion and adjustable zero, for providing an indication of the pressure;
a catheter adapted to extend to such locations from outside such patient's body and having:
a first portion which, when the catheter is in use, in within such patient's body and distal with respect to the circuitry means,
a second portion which, when the catheter is in use, is outside such patient's body and proximal with respect to the circuitry means, and
at least two lumens defined within the catheter and communicating between its proximal and distal portions;
a pressure transducer in the first portion of the catheter, the circuitry means being responsive to the transducer; the pressure transducer having a measurement side that is exposed to the distal end of a first one of the two lumens;
the first one of the two lumens being sealed at the distal portion against the pressure outside the catheter; and
the other one of the two lumens being exposed at the distal portion to the pressure outside the catheter; and
means for selectively connecting the first one of the two lumens, in its proximal portion, for communication with either;
atmospheric pressure, for measurement of such gauge pressure within such patient's body, or
a known pressure source, to facilitate calibrating the scale expansion of the apparatus.

21. The apparatus of claim 20, further comprising:
automatic means, responsive to the electronic circuitry means when the connecting means is connected for communication with atmospheric pressure, and also responsive to the electronic circuitry means when the connecting means is connected for communication with a known pressure source, for calibrating the electronic-circuitry scale expansion for consistency with the magnitude of the known pressure in conjunction with a desired calibration factor.

22. The apparatus of claim 20, further comprising:
a pressure-measuring means for connection to the proximal portion of said other one of the two lumens, for independently measuring the mean pressure therein;
means for determining a mean value of the indication of the electronic circuitry means; and
means for comparing the mean value of the indication of the electronic-circuitry means and the independently measured mean pressure.

23. The apparatus of claim 22, further comprising:
automatic means, responsive to the comparing means, for adjusting the zero of the electronic circuitry means in such a way as to substantially eliminate discrepancy between the means value and the mean pressure.

24. The apparatus of claim 22, wherein:
the pressure-measuring means measures the mean pressure over a time interval that is:
long compared with major fluctuations in such pressure, if such fluctuations are substantially nonperiodic, or
substantially equal to an integral number of periods, if such pressure fluctuates substantially periodically.

25. The apparatus of claim 22, wherein:
the mean-value-determining means determines the mean value of the electronci-circuitry indication over a time interval that is:
long compared with major fluctuations in the indication, if the flutuations are substantially nonperiodic, or
substantially equal to an integral number of periods, if the indication fluctuates substantially periodically.

26. The appaatus of claim 20, wherein:
the first one of the two lumens is, in its proximal portion, connecting to a reference-pressure selector stopcock means for selectively making pressure connection to either a known pressure source or to atmospheric pressure.

27. In a method of zeroing a catheter-tip pressure transducer system having a catheter tipped with a pressure-sensitive diaphragm in pressure contact with living tissue, and having an adjustable-zero scale display apparatus responsive to the diaphragm, the method being applying a reference pressure to the diaphragm of the transducer system; then observing the signal of the display apparatus responsive to the reference pressure; then zeroing the display apparatus at the reference pressure by bringing the signal into registry with a base line representing zero upon a scale;

an improvement to the zeroing of said method comprising:

independently of the diaphragm, measuring the pressure on the diaphragm at the point of its pressure contact with living tissue; and zeroing the display apparatus at the reference pressure by bringing the signal into registry with the level of the independently measured pressure upon the scale.

28. The method improvement according to claim 27 further comprising:

calibrating said transducer system prior to the zeroing.

29. The method improvement according to claim 27 further comprising:

measuring the mean pressure of the diaphragm; and wherein said zeroing further comprises:

zeroing by bringing the mean value of the signal into registry with the independently measured mean pressure.

* * * * *

UNITED STATES PATENT AND TRADEMARK OFFICE
CERTIFICATE OF CORRECTION

PATENT NO. : 4,672,974
DATED : June 16, 1987
INVENTOR(S) : Arnold St. J. Lee

Page 1 of 2

It is certified that error appears in the above-identified patent and that said Letters Patent is hereby corrected as shown below:

Column 7, line 3, change the spelling of "sensivitivy" to "sensitivity."

Column 9, line 10, change the spelling of "diapgragm" to "diaphragm."

Column 10, line 47, change the spelling of "cathether-tip" to "catheter-tip."

Column 14, lines 40 and 41, change the spelling of "catherer-tip" to "catheter-tip"; and lines 45 and 46, change the spelling of "haivng" with "having"; and "diamphragm" to "diaphragm."

Column 16, line 59, change the spelling of "idaphragm" to "diaphragm."

Column 17, line 1, correct the typographical error "tO" by replacement with "to."

Column 18, line 55, change the spelling of "electronci-circuitry" to "electronic-circuitry";

UNITED STATES PATENT AND TRADEMARK OFFICE
CERTIFICATE OF CORRECTION

PATENT NO. : 4,672,974
DATED : June 16, 1987
INVENTOR(S) : Arnold St. J. Lee

It is certified that error appears in the above-identified patent and that said Letters Patent is hereby corrected as shown below:

and line 63, change the spelling of "appaatus" to "apparatus".

Signed and Sealed this

Tenth Day of November, 1987

Attest:

DONALD J. QUIGG

*Attesting Officer*  *Commissioner of Patents and Trademarks*